United States Patent
Urbanczyk et al.

(10) Patent No.: US 11,287,413 B2
(45) Date of Patent: Mar. 29, 2022

(54) METHOD FOR DETERMINING A PLASTICITY PARAMETER OF A HYDRATING CEMENT PASTE

(71) Applicant: TOTAL SE, Courbevoie (FR)

(72) Inventors: Christophe Urbanczyk, Pau (FR); André Garnier, Montardon (FR); Jean Sulem, Paris (FR); Siavesh Ghabezloo, Bry sur Marne (FR); Nicolaine Agofack, Trondheim (NO)

(73) Assignee: TOTAL SE, Courbevoie (FR)

( * ) Notice: Subject to any disclaimer, the term of this patent is extended or adjusted under 35 U.S.C. 154(b) by 0 days.

(21) Appl. No.: 16/093,887

(22) PCT Filed: Apr. 15, 2016

(86) PCT No.: PCT/IB2016/000645
§ 371 (c)(1),
(2) Date: Oct. 15, 2018

(87) PCT Pub. No.: WO2017/178860
PCT Pub. Date: Oct. 19, 2017

(65) Prior Publication Data
US 2019/0107526 A1    Apr. 11, 2019

(51) Int. Cl.
*G01N 33/00* (2006.01)
*G01N 33/38* (2006.01)
(Continued)

(52) U.S. Cl.
CPC .......... *G01N 33/383* (2013.01); *G01N 3/08* (2013.01); *G01N 3/62* (2013.01); *G01N 11/00* (2013.01); *G01N 2203/0094* (2013.01)

(58) Field of Classification Search
CPC .......... G01N 33/383; G01N 3/08; G01N 3/62; G01N 11/00; G01N 2203/0094
(Continued)

(56) References Cited

U.S. PATENT DOCUMENTS 5,541,855 A * 7/1996 Enzler ............... G01N 11/14
                                                    366/142
7,849,650 B2 * 12/2010 Tonyan ............. B32B 3/06
                                                    106/735
(Continued)

FOREIGN PATENT DOCUMENTS

WO   WO 2015/143368 A1   9/2015
WO   WO 2017/178858      10/2017

OTHER PUBLICATIONS

PCT International Search Report for PCT/IB2016/000645, dated Aug. 10, 2016, 3 pages.
(Continued)

*Primary Examiner* — Max H Noori
(74) *Attorney, Agent, or Firm* — Patterson Thuente Pedersen, P.A.

(57) ABSTRACT

A method for determining a plasticity parameter of a hydrating, cement paste by mixing the components to obtain a cement slurry, pouring the cement slurry in a scaled oedometric cell, and performing an oedometric measurement operation within a predefined early-age time interval by applying a predefined axial stress path to the cement slurry over a predefined measurement duration and measuring an axial strain. A plasticity parameter of the hydrating cement paste is determined b a calibration processing operation comprising providing an initial value of a plasticity parameter of an elastoplastic model of hydrating cement paste, determining simulated axial strain values by solving the elastoplastic model of hydrating cement and comparing the simulated axial strain values with the axial strain measurements of the cement slurry.

11 Claims, 3 Drawing Sheets

(51) Int. Cl.
*G01N 3/08* (2006.01)
*G01N 11/00* (2006.01)
*G01N 3/62* (2006.01)

(58) Field of Classification Search
USPC .......................................................... 73/893
See application file for complete search history.

(56) References Cited

U.S. PATENT DOCUMENTS

| | | | | |
|---|---|---|---|---|
| 8,794,078 | B2* | 8/2014 | Darbe | G01N 33/383 |
| | | | | 73/803 |
| 9,803,523 | B2* | 10/2017 | Hagg | C04B 41/85 |
| 2002/0057095 | A1* | 5/2002 | Zoughi | G01N 22/00 |
| | | | | 324/646 |
| 2005/0138991 | A1 | 6/2005 | Wallevik et al. | |
| 2005/0210995 | A1* | 9/2005 | Drnevich | C04B 28/02 |
| | | | | 73/803 |
| 2008/0178683 | A1* | 7/2008 | Heathman | G01N 3/24 |
| | | | | 73/803 |
| 2008/0233044 | A1 | 9/2008 | Hansen et al. | |
| 2012/0158333 | A1 | 6/2012 | Li et al. | |
| 2013/0192382 | A1 | 8/2013 | Bois et al. | |
| 2014/0007695 | A1 | 1/2014 | Darbe | |
| 2015/0033862 | A1 | 2/2015 | Bois et al. | |
| 2017/0183269 | A1* | 6/2017 | Pearl, Jr. | C04B 28/02 |
| 2018/0258337 | A1* | 9/2018 | Contreras | C04B 28/02 |

OTHER PUBLICATIONS

PCT Written Opinion of the ISA for PCT/IB2016/000645, dated Aug. 10, 2016, 6 pages.

M. Thiercelin et al: "A Soil Mechanics Approach to Predict Cement Sheath Behavior", SPE/ISRM Rock Mechanics in Petroleum Engineering, Jul. 10, 1998 (Jul. 10, 1998), XP055292313, DOI: 10.2118/47375-MS.

Ghabezloo S. (2011) "*Micromechanics analysis of thermal expansion and thermal pressurization of a hardened cement paste*", Cement and Concrete Research, 2011, 41(5), 520-532,DOI 10.1016/j.cemconres.2011.01.023.

European Office Action from EP Application 16724106.6, dated Nov. 13, 2019, 4 pgs.

Office Action from GCC Application No. GC 2017-33208 dated Dec. 13, 2018,4 pgs.

PCT International Search Report for PCT/IB2016/000608, dated Nov. 30, 2016, 2 pages.

PCT Written Opinion of the ISA for PCT/IB2016/000608, dated Nov. 30, 2016, 6 pages.

Nicolaine Agofack: "Comportement des ciments pétroliers au jeune âge et intégrité des puits", Jan. 1, 2016 (Jan. 1, 2016), XP055321461, Paris Retrieved from the Internet: URL:www.theses.fr/2015PESC1040/abes [retrieved on Nov. 21, 2016] abstract 252 pages.

« Effets des contraintes et de la température sur l'intégrité des ciments des puits pétroliers », Manh Huyen VU, 23 fevrier 2012, 241 pages.

Application and file history from U.S. Appl. No. 16/093,920, filed Oct. 15, 2018, inventors Urbanczyk et al.

Behrmann, L. A., Li, J. L., Venkitaraman, A. & Li, H., 1997. Borehole Dynamics During Underbalanced Perforating. Society of Petroleum Engineers, Issue SPE 38139, pp. 17-24.

Thiercelin, M. J., Dargaud, B., Baret, J. F. & Rodriguez, W. J., 1997. Cement Design Based on Cement Mechanical Response. Society of Petroleum Engineers, Issue SPE 38598, pp. 337-348.

American Petroleum Institute, "Isolating Potential Flow Zones During Well Construction", API Standard 65—Part 2, Second Edition, Dec. 2010, 96 pgs.

\* cited by examiner

METHOD FOR DETERMINING A PLASTICITY PARAMETER OF A HYDRATING CEMENT PASTE

RELATED APPLICATIONS

The present application is a National Phase entry of PCT Application No. PCT/IB2016/000645, filed Apr. 15, 2016, said application being hereby incorporated by reference herein in its entirety.

FIELD OF THE INVENTION

The present invention relates to the domain of cement slurry hydration and especially during drilling operations.

BACKGROUND OF THE INVENTION

The approaches described in this section could be pursued, but are not necessarily approaches that have been previously conceived or pursued. Therefore, unless otherwise indicated herein, the approaches described in this section are not prior art to the claims in this application and are not admitted to be prior art by inclusion in this section. Furthermore, all embodiments are not necessarily intended to solve all or even any of the problems brought forward in this section.

A cement sheath is an essential part of an oil or gas well located between the casing of the well and surrounding geological formations. Cement sheaths provide zonal isolation of different fluids along the well to seal permeable formations, protect the casing against corrosion and provide mechanical support.

A loss of integrity of a cement-sheath may result in the pressurization of annulus, fluid communication between drilled geological formations or fluid communication to annuli, contamination of groundwater and the pathway of fluids (oil, gas and water) to surface, and, in catastrophic cases, in a blowout and in the total damage of the infrastructure.

To form a cement sheath, cement slurry is pumped between a casing run in the well and the geological formations and is let to harden over time to result in a solid sheath.

However, during the life of a well, from drilling to completion, production or injection till P&A (plug and abandonment), a cement sheath is submitted to various mechanical and thermal loadings that can potentially damage it and alter its performance.

Moreover, some of these loadings are applied at very early age, when the mechanical properties of the cement sheath are not yet sufficiently developed.

One example of such an early-age loading is a casing test used to check there is no leak. The applied pressure during a casing test can vary from a few tens of MPa in normally pressurized reservoirs to more than 100 MPa in high pressure reservoirs. The thermal and or mechanical stresses can damage the cement and alter its key properties. For example, it may result in:

(a) debonding or separation between the cement sheath and the casing or between the cement sheath and geological formations, which can lead to the creation of micro-annular or channel;

(b) the creation of fractures in the cement sheath.

Unfortunately, very little is known about the effect of such early-age mechanical loading and unloading on the future mechanical behavior and state of the cement sheath.

Indeed, with existing conventional apparatus and method, it is difficult to measure the parameters of the cement slurry at an early age. While the cement is usually hydrated under a predefined temperature and pressure, the specimens have to be brought to "ambient" conditions prior to measure its mechanical properties: this process modify the mechanical properties of the cement.

There is thus a need to develop a novel way for calibrating and measuring mechanical parameters from a cement paste during its hydration in order to be able to predict the response of the existing cement sheath in oil wells under various loadings.

SUMMARY OF THE INVENTION

To this aim, a first object of the invention is a method for determining a plasticity parameter of a hydrating cement paste comprising:
  providing a plurality of components of a cement paste comprising at least cement powder and water,
  mixing said plurality of components to obtain a cement slurry and pouring said cement slurry in a sealed oedometric cell,
  performing at least one oedometric measurement operation comprising:
    applying a predefined axial stress path to the cement slurry inside the oedometric cell over a predefined measurement duration, and
    performing a plurality of measurements of an axial strain of said cement slurry inside the oedometric cell, respectively at a plurality of respective sample times within said predefined measurement duration,
  wherein said at least one oedometric measurement operation is performed within a predefined early-age time interval following the mixing of said cement slurry,
  determining at least one value of a plasticity parameter of the hydrating cement paste by
    performing at least one calibration processing operation comprising:
      providing an initial value of a plasticity parameter of an elastoplastic model of hydrating cement paste,
      determining a plurality of simulated axial strain values by solving said elastoplastic model of hydrating cement paste for a plurality of respective axial stress conditions respectively corresponding to axial stress values of the predefined axial stress path at the respective sample times of the plurality of axial strain measurements of the cement slurry, and
    comparing the plurality of simulated axial strain values from said at least one calibration processing operation with the plurality of axial strain measurements of the cement slurry to determine a plasticity parameter of the hydrating cement paste.

In some embodiments, one might also use one or more of the following features:
  said predefined early-age time interval following the mixing of said cement is less than 10 days, preferably less than 6 days;
  said predefined axial stress path is a constant axial stress over the predefined measurement duration;
  said predefined measurement duration is at least 1 day, preferably at least 4 days, more preferably 6 days;
  said oedometric measurement operation starts less than 10 minutes after the mixing of said cement slurry;
  said predefined axial stress path comprises at least one loading/unloading cycle in which an axial stress applied to the cement slurry varies between a predefined minimum axial stress and a predefined maximum axial stress;

said predefined measurement duration is less than 1 hour;

said plasticity parameter is chosen between a parameter of a hardening function, a parameter of a plastic yield surface and a parameter of a plastic potential of said elastoplastic model of hydrating cement paste;

solving said elastoplastic model of hydrating cement paste comprises computing a plastic yield surface of a modified Cam-Clay yield surface model by solving:

$$q^2+M^2(p_d+p_t)(p_d-p_0)=0$$

Where $p_d$ is the differential mean stress (Terzaghi effective mean stress)

$p_t$ is the yield stress related to the tensile strength of the material $p_0$ is the yield stress under hydrostatic loading M is the Cam-Clay parameter corresponding to the slope of the Critical State Line and said plasticity parameter is a function of said Cam-Clay parameter M;

solving said elastoplastic model of hydrating cement paste comprises computing a hardening function of the plastic yield surface by solving:

$$dp_0-h_\xi d\xi-h_t d\varepsilon_{vp}=0$$

Where $\xi$ is the hydration degree $\varepsilon_{vp}$ is the plastic volumetric strain $h_\xi=(\partial p_0)/\partial \xi$ and $h_t=(\partial p_0)/(\partial \varepsilon_{vp})$ are hardening parameters and wherein said plasticity parameter is a function of at least one of said hardening parameter $h_\xi$ and $h_t$;

solving said elastoplastic model of hydrating cement paste further comprises computing a poroelasticity of a cement paste derived from Hooke's law by solving:

$$c_d dp_d+c_d(1-b)\chi dp_w-(d\varepsilon_v-d\varepsilon_{vp})=0$$

$$dq-G(d\gamma-d\gamma_p)=0$$

Where $p_d$ is the differential mean stress (Terzaghi effective mean stress)

$p_w$ is the pore pressure q is the second invariant of the deviatoric stress tensor $\gamma$ is the shear strain intensity $\gamma_p$ is plastic shear strain intensity $\varepsilon_v$ is the volumetric strain $\varepsilon_{vp}$ is the plastic volumetric strain $c_d=1/K_d$ is the drained compressibility of the porous material b is Biot's effective stress coefficient $\chi$ is the Bishop effective stress coefficient G is the elastic shear modulus and wherein said poroelasticity parameters $c_d$, b, $\chi$ and G are determined by using an upscaling technique;

said calibration processing operation is repeated a plurality of times with a respective plurality of initial values of the plasticity parameter, said plurality of initial values of the plasticity parameter scanning a predefined range of initial value of the plasticity parameter, and wherein comparing the plurality of simulated axial strain values from said plurality of calibration processing operations with the plurality of axial strain measurements of the cement slurry comprises computing a plurality of error values, respectively associated to each simulated axial strain values and the value of the plasticity parameter may be determined from said plurality of error values, in particular by selecting the initial value of the plasticity parameter leading to the smallest error value among the plurality of error values.

Another object of the invention is a non-transitory computer readable storage medium, having stored thereon a computer program comprising program instructions, the computer program being loadable into a data-processing unit and adapted to cause the data-processing unit to carry out the steps of a method as described above when the computer program is run by the data-processing device.

Other features and advantages of the method and apparatus disclosed herein will become apparent from the following description of non-limiting embodiments, with reference to the appended drawings.

BRIEF DESCRIPTION OF THE DRAWINGS

The present invention is illustrated by way of example, and not by way of limitation, in the figures of the accompanying drawings, in which like reference numerals refer to similar elements and in which.

DETAILED DESCRIPTION OF THE DRAWINGS

Figure 4:
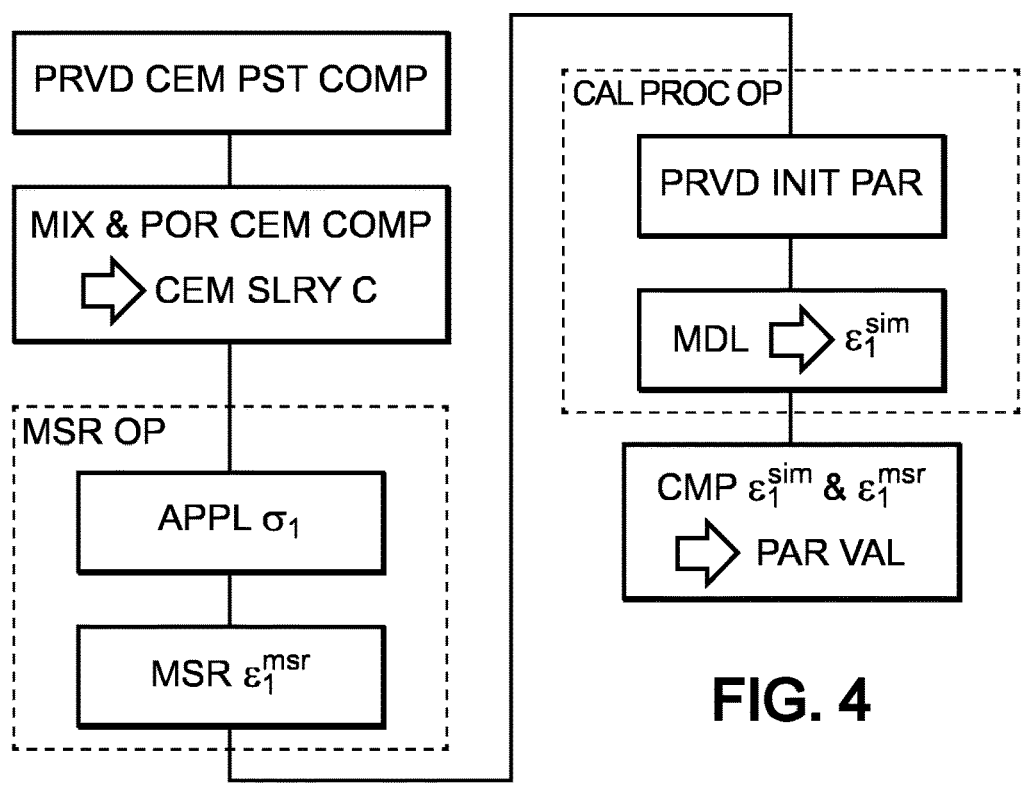
FIG. 4 is a flow chart describing an embodiment of a method for determining a plasticity parameter of a hydrating cement paste according to the invention.

FIG. 4 is a flow chart describing an embodiment of a method for determining a plasticity parameter of a hydrating cement paste according to the invention.

Figure 5:
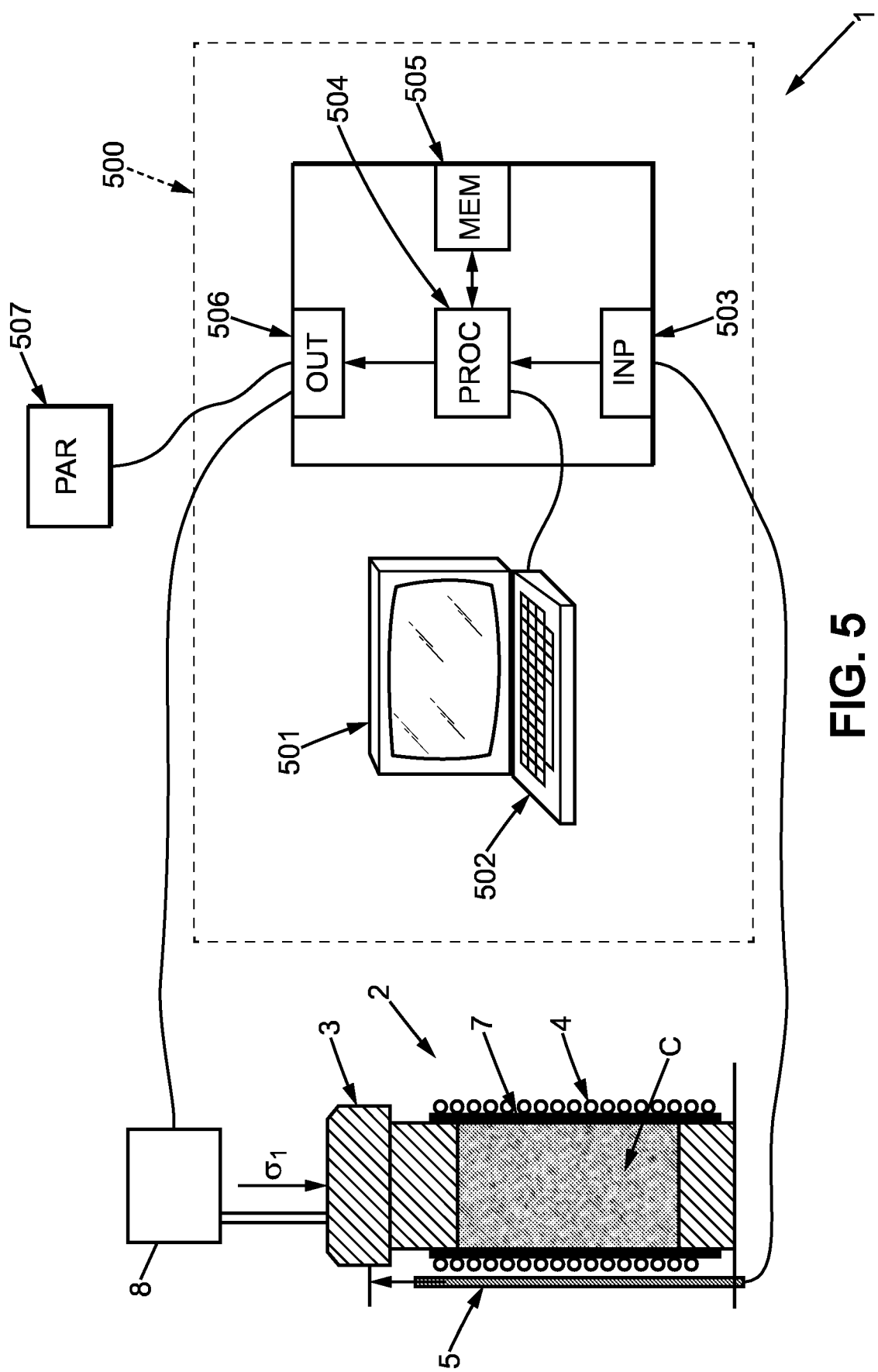
FIG. 5 illustrates a possible embodiment for a measurement device that enables the present invention.

Such a method may be conducted with a measurement device 1 as illustrated on FIG. 5.

In a first step of the method, components of a cement paste are provided.

A cement paste comprises a plurality of components, mainly cement powder and water but also, optionally, a number of additives.

A cement powder may for instance be a class G cement powder with a chemical composition in accordance with the American Petroleum Institute (API) 10A or ISO 10426-1 requirements for class G cements. Water may be for instance distilled and deaerated water but may also be other types of water such as salted water or saturated water. Additives may comprise anti-foaming, dispersing and anti-settling additives for instance. In one particular and non-limitative example, the cement powder of water ratio w/c may for instance be 0.44.

The provided components of the cement paste may be similar to component of a cement paste used in a real well, in a real and industrial scenario.

The components of the cement paste are then mixed to obtain cement slurry.

To this aim, water is for instance poured into a mixing container, which is then placed on a mixer base. The dry anti-settling agent may then be added to the water and a motor of the mixer base can be turned on and maintained to, for example, 500±50 rotations per minutes for 5 minutes of agitation. The liquid anti-foaming and dispersing additives are then added to the mixing water. The cement powder is added under 4000±200 rotations per minutes, for instance in 15±1 second. The speed of the motor of the mixer base can then be increased to about 12 000±500 rotations per minute and mixing may end automatically after 35±1 second. The durations and rotation speeds mentioned before are stated only for illustrative purposes and should not be understood as limiting the invention in any way.

The cement slurry can then be mixed, poured into an oedometric cell 2 of a measurement device 1. The cement slurry C contained in the oedometric cell, can for instance present dimensions of 50.3 mm in diameter and 85 mm in height. The mass of cement slurry C in the oedometric cell may be between 300-350 g. The measurements described hereafter may be conducted without supplying additional water during hydration.

The measurement device 1 is illustrated on FIG. 5 and comprises for instance an oedometric cell 2, an axial frame 3 able to apply axial stress on the slurry in the oedometric cell, a cooling heating system 4 to control the temperature of the slurry in the oedometric cell, a sensor 5 to measure the axial strain of the cement slurry inside the oedometric cell and a control unit 500 to control the axial frame 3. The cooling heating system 4 and the sensor 5 perform the method according to the invention.

It should be noted that the control unit 500 is illustrated on FIG. 5 as a single computer device but may be spread across, or separated into, multiple components or computer devices, each performing only one or several steps of the method according to the invention.

In this embodiment, the control unit 500 comprises a computer, this computer comprising a memory 505 to store program instructions loadable into a circuit and adapted to cause circuit 504 to carry out the steps of the present invention when the program instructions are run by the circuit 504.

The memory 505 may also store data and useful information for carrying the steps of the present invention as described above.

The circuit 504 may be for instance:
a processor or a processing unit adapted to interpret instructions in a computer language, the processor or the processing unit may comprise, may be associated with or be attached to a memory comprising the instructions, or
the association of a processor/processing unit and a memory, the processor or the processing unit adapted to interpret instructions in a computer language, the memory comprising said instructions, or
an electronic card wherein the steps of the invention are described within silicon, or
a programmable electronic chip such as a FPGA chip (for "Field-Programmable Gate Array").

This computer comprises an input interface 503 for the reception of data and measurements used for the above method according to the invention and an output interface 506 for providing the plasticity parameter determined by the method and for controlling the various components of the measurement device 1, in particular the axial frame 3, the cooling heating system 4 and the sensor 5.

To ease the interaction with the computer, a screen 501 and a keyboard 502 may be provided and connected to the computer circuit 504.

The axial frame 3 can be able to apply over 600 kN to the cement slurry C contained in the oedometric cell 2, for instance by using an electromechanical ram controlled by movidrives 8.

The oedometric cell 2 is a sealed cell so that pressure can be applied to the cement slurry even when said slurry is in a liquid or fluid state without losing part of the sample. The cement paste can thus be submitted to a mechanical unloading/loading cycles before the setting time of the cement. The oedometric cell 2 comprises for instance a hollow cylinder 7 made of steel, for instance a cylinder with a 50.3 mm internal diameter, a 90 mm external diameter and a 125 mm height. The hollow cylinder can in particular be able to support a pressure of over 120 MPa applied on its inner surface while staying in its elastic domain.

The hollow cylinder 7 can be surrounded by a cooling/heating system 4 comprising small-diameter tubings connected to a cryostat in which cold/hot fluid at a controlled temperature circulates.

The sensor 5 can be used to measure the axial strain of the sample. The sensor 5 may for instance be a linear variable differential transformer (LVDT) sensor. The sensor 5 can be arranged along the hollow cylinder. The hollow cylinder 7 may be able to move freely in order to reduce the effects of friction between the sample and said hollow cylinder 7, hence ensuring that the displacements measured by the sensor 5 only correspond to the displacements that exist in the sample.

During the method according to the invention, the oedometric cell 2 may be cooled or heated to a test temperature before preparing the cement slurry to ensure a stable and homogeneous temperature inside the cell.

The measurement device 1 can be used to perform at least one oedometric measurement operation.

An oedometric measurement operation involves applying a predefined axial stress path to the cement slurry inside the oedometric cell over a predefined measurement duration, and performing a plurality of measurements of an axial strain of said cement slurry inside the oedometric cell at a plurality of respective sample times within said predefined measurement duration.

The oedometric measurement operation is performed within a predefined early-age time interval following the mixing of said cement slurry.

The predefined early-age time interval following the mixing of said cement is less than 10 days, preferably less than 6 days. This way the measurements are conducted on a hydrating cement paste, thereby allowing the determination of plastic parameters.

The predefined axial stress path is applied to the cement slurry inside the oedometric cell 2 by using the axial frame 3.

A predefined temperature path may also be applied to the cement slurry inside the oedometric cell 2 by using the cooling heating system 4.

By "predefined axial stress path" and "predefined temperature path", it is respectively meant a profile of axial stress and temperature applied to the cement slurry over the predefined measurement duration.

Figure 1:
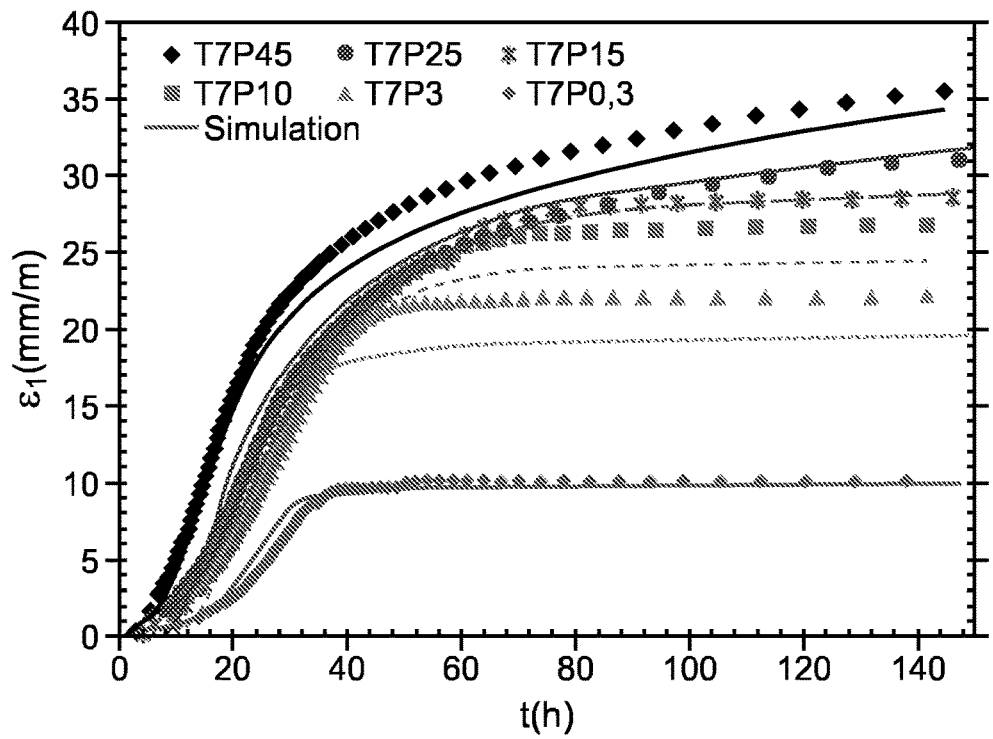
FIG. 1 is a graph illustrating examples of measurements of axial strains (points) with predefined axial stress paths being constant axial stress, together with simulated axial strain values (lines).
Figure 2:
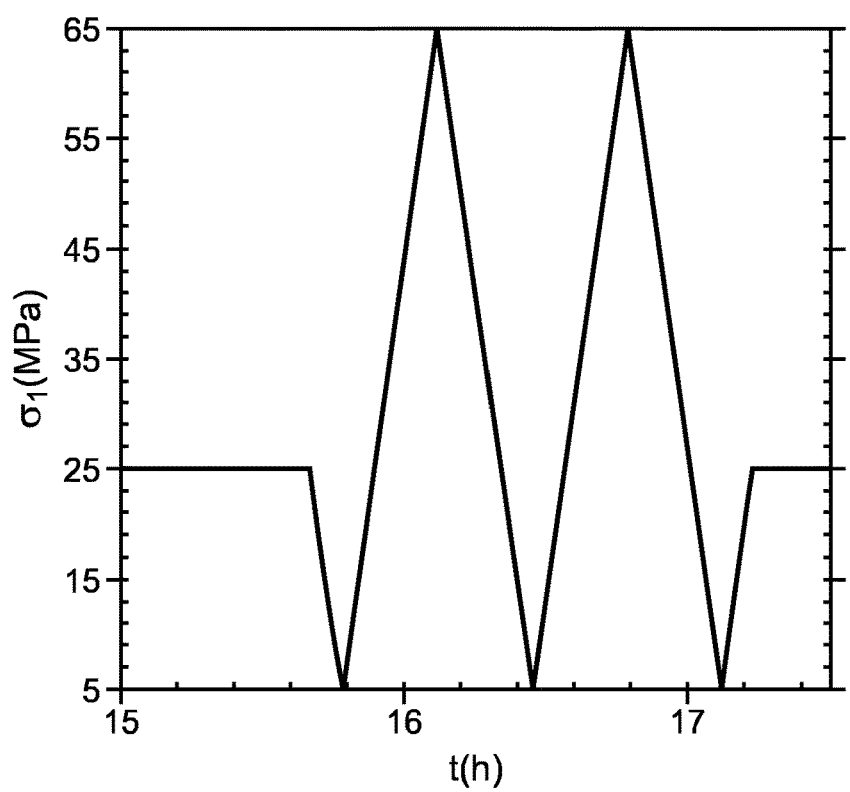
FIG. 2 is a graph illustrating a predefined axial stress path comprising two consecutive loading/unloading cycles extending between a minimal axial stress of 5 MPa and a maximal axial stress of 65 MPa, each cycle being conducted over a measurement duration of less than one hour.

Several predefined axial stress paths and predefined temperature path may be used, and are illustrated on FIGS. 1 and 2

In a first embodiment illustrated on FIG. 1, a predefined axial stress path may be a constant axial stress over the predefined measurement duration. For instance, a constant axial stress of 45 MPa over a duration of six days is illustrated on FIG. 1.

The predefined temperature path may also be constant over the predefined measurement duration. For instance, a constant temperature of 7° C. over a duration of six days is illustrated on FIG. 1.

In this embodiment, the predefined measurement duration may be at least 1 day, preferably at least 4 days, more preferably 6 days. This way, the hydration degree of the cement slurry increases over a measurable range during the predefined measurement duration.

In this embodiment, the oedometric measurement operation may start less than 10 minutes following the mixing of said cement slurry, in particular less than 5 minutes following the mixing of said cement slurry. It is thus possible to have access to the very early behavior of the cement slurry during hydration which, as the inventors have discovered, is important to obtain a reliable calibration of the parameters of the cement paste.

Figure 3:
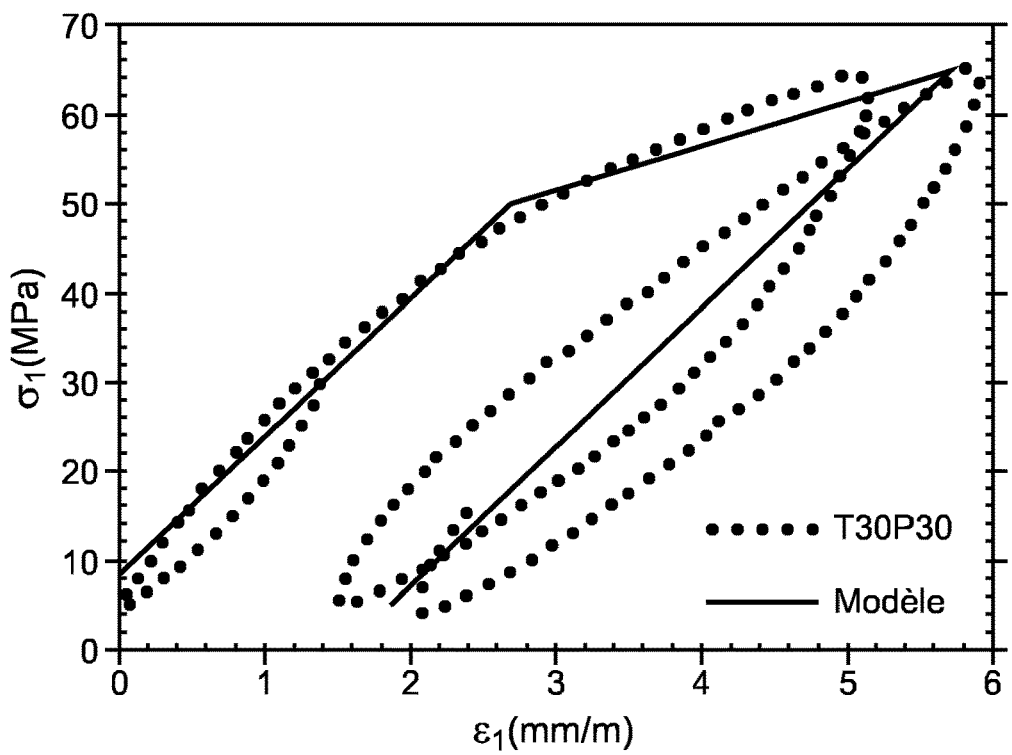
FIG. 3 is a graph illustrating measurements of axial strains (points) with the predefined axial stress path similar illustrated on FIG. 2, i.e. comprising two consecutive loading/unloading cycles extending between a minimal axial stress of 5 MPa and a maximal axial stress of 65 MPa, together with simulated axial strain values (lines).

In a second embodiment illustrated in FIGS. 2 and 3, the predefined axial stress path may comprise at least one loading/unloading cycle. A loading/unloading cycle is a cycle in which an axial stress applied to the cement slurry varies between a predefined minimum axial stress and a predefined maximum axial stress.

In this embodiment, the predefined measurement duration may be short, in particular less than one hour. This way, the hydration degree of the cement slurry can be considered constant.

In this embodiment, the predefined temperature path may also be constant over the predefined measurement duration, for instance, a constant temperature of 7° C. over the predefined measurement duration.

During the oedometric measurement operation, a plurality of measurements of an axial strain of said cement slurry inside the oedometric cell can be performed at a plurality of respective sample times within said predefined measurement duration.

Such a plurality of measurements is illustrated on FIGS. 1 and 3.

The measurements may be periodically performed over the predefined measurement duration when the test temperature and axial stress is reached. For instance, measurements can be performed every 5 or 30 seconds.

Each measurement can comprise a value of axial strain, a value of applied axial stress and an associated sample time.

The graphs of FIG. 1 shows examples of measurements of axial strains (points) with predefined axial stress paths being constant axial stress, together with simulated axial strain values (lines) that are detailed later:

the curve C-T7P45 is curve illustrating the hydration of a cement slurry at 7° C. and for 45 MPa.
the curve C-T7P10 is curve illustrating the hydration of a cement slurry at 7° C. and for 10 MPa.
the curve C-T7P25 is curve illustrating the hydration of a cement slurry at 7° C. and for 25 MPa.
the curve C-T7P3 is curve illustrating the hydration of a cement slurry at 7° C. and for 3 MPa.
the curve C-T7P1.5 is curve illustrating the hydration of a cement slurry at 7° C. and for 1.5 MPa.

the curve C-T7P0.3 is curve illustrating the hydration of a cement slurry at 7° C. and for 0.3 MPa.

The graph of FIG. 2 shows an example of a predefined axial stress path comprising two consecutive loading/unloading cycles extending between a minimal axial stress of 5 MPa and a maximal axial stress of 65 MPa, each cycle being conducted over a measurement duration of less one hour.

The graph of FIG. 3 shows an example of measurements of axial strains (points) with the predefined axial stress path similar illustrated on FIG. 2, i.e. comprising two consecutive loading/unloading cycles extending between a minimal axial stress of 5 MPa and a maximal axial stress of 65 MPa, together with simulated axial strain values (lines) that are detailed later.

Following the completion of said oedometric measurement operation, the method according to the invention comprises a step of determining at least one parameter of an elastoplastic model of hydrating cement paste from said plurality of axial strain measurements of the cement slurry by performing at least one calibration processing operation.

The parameter may in particular be a plasticity parameter as detailed hereafter.

To this aim, a elastoplastic model of hydrating cement paste may be provided and comprise a set of equations. Said set of equations may in turn comprise at least a first set of equations function of a poroelasticity of a cement paste and a second set of equations function of a plasticity of a cement paste.

The expression "set of equations" is used in the present description but it should be noted that such a set may comprise, in some case, a single equation and should not be understood as being restricted to a plurality of equations.

Moreover, only a limited number of equations are detailed in the present disclosure for the sake of brevity, but additional equations may be included in the elastoplastic model of hydrating cement paste as known in the field of the invention. Examples of such additional equations are equations defining boundary conditions, conservation of matter or formal equations defining parameters and variables of the model.

Such formal equations may be for instance the definitions of strain and stress tensor as known in continuum mechanics. In axisymmetric conditions, the strain tensor can be defined in terms of the volumetric strain ($\varepsilon_v$) and the shear strain ($\gamma$) from the axial strain ($\varepsilon_1$) and radial strain components ($\varepsilon_3$). It is further decomposed into an elastic part and a plastic part that can be written as:

$$\begin{cases} \varepsilon_v = \varepsilon_1 + 2\varepsilon_3 = \varepsilon_{ve} + \varepsilon_{vp} & (a) \\ \gamma = \dfrac{2|\varepsilon_1 - \varepsilon_3|}{\sqrt{3}} = \gamma_e + \gamma_p & (b) \end{cases}$$

The stress tensor may also be decomposed into a spherical part and a deviatoric part.

As mentioned above, a first set of equations is a function of a poroelasticity of a cement paste.

An example of such a first set of equation $g_1$, $g_2$ may be derived from Hooke's law, in the case of a poroelastic material and written as (see Coussy (2004), "*Poromechanics*", Wiley:

$$g_1: c_d dp_d + c_d(1-b)\chi dp_w - (d\varepsilon_v - d\varepsilon_{vp}) = 0$$

$$g_2: dq - G(d\gamma - d\gamma_p) = 0$$

Where
p_d is the differential mean stress (Terzaghi effective mean stress)
p_w is the pore pressure
q is the second invariant of the deviatoric stress tensor
γ is the shear strain intensity
γ_p is plastic shear strain intensity
ε_v is the volumetric strain
ε_vp is the plastic volumetric strain
$c_d=1/K_d$ is the drained compressibility of the porous material
b is Biot's effective stress coefficient
χ is the Bishop effective stress coefficient
G is the elastic shear modulus The poroelasticity parameters $c_d$, b, χ and G may for instance be determined by using an upscaling technique. An upscaling technique that can be used in the present case is detailed in Ghabezloo S. (2011) "*Micromechanics analysis of thermal expansion and thermal pressurization of a hardened cement paste*", Cement and Concrete Research, 2011, 41(5), 520-532, DOI 10.1016/j.cemconres.2011.01.023.

A second set of equations of the elastoplastic model of hydrating cement paste may be function of the plasticity of the cement paste. The second set of equations may comprise at least one equation defining a plastic yield surface F and/or a plastic potential Q.

A yield function defining a plastic yield surface F can be for instance derived from a modified Cam-Clay model and written as:

$$F=q^2+M^2(p_d+p_t)(p_d-p_0)$$

Where
p_d is the differential mean stress (Terzaghi effective mean stress)
p_t is the yield stress related to the tensile strength of the material
p_0 is the yield stress under hydrostatic loading
M is the Cam-Clay parameter corresponding to the slope of the Critical State Line An equation $g_3$ of the elastoplastic model of hydrating cement paste may be straightforwardly derived from the above written yield function and written as:

$$g_3: q^2+M^2(p_d+p_t)(p_d-p_0)=0$$

$p_0$ depends from the hydration degree and the plastic deformations in the cement paste. This dependence may be written as:

$$\begin{cases} p_0 = p_0(\xi, \varepsilon_{vp}) \\ dp_0 = \frac{\partial p_0}{\partial \xi} d\xi + \frac{\partial p_0}{\partial \varepsilon_{vp}} d\varepsilon_{vp} \end{cases}$$

A hardening function of the plastic yield surface can thus be written as:

$$g_4: dp_0 - h_\xi d\xi - h_t d\varepsilon_{vp} = 0$$

Where
ξ is the hydration degree
ε_vp is the plastic volumetric strain
$h_\xi = \partial p_0/\partial \xi$ and $h_t = \partial p_0/\partial \varepsilon_{vp}$ are hardening parameters The second set of equations may then also comprise said equation $g_4$ of a hardening function of the plastic yield surface.

The plasticity parameters M, $h_\xi$ and $h_t$ of the second set of equations $g_3$, $g_4$ are essential to define the mechanical behavior of the hydrating cement paste.

However, these plasticity parameters cannot be easily measured on the cement paste.

To this aim, the method according to the invention involve a step of determining at least one plasticity parameter of the hydrating cement paste by performing at least one calibration processing operation.

It should be noted that the plasticity parameter may be said one of said parameters M, $h_\xi$ and $h_t$ of the second set of equations or a function of said parameters but may also be another parameter of a plastic yield surface of a model of hydrating cement paste, in particular if said model comprises additional equations. For instance, the plasticity parameter may be a parameter of a plastic potential of said elastoplastic model of hydrating cement paste if such a plastic potential is considered to differ from the yield function of the plastic yield surface.

A calibration processing operation of the method is illustrated on FIG. 4 and may begin with a sub-operation in which an initial value of a plasticity parameter of the elastoplastic hydrating cement paste model is provided.

The initial value of the plasticity parameter may be obtained from a previously performed calibration processing operation or may be an initial guess.

The calibration processing operation then comprises a sub-operation in which a plurality of simulated axial strain values are determined. The plurality of simulated axial strain values can be determined by solving the elastoplastic hydrating cement paste model for a plurality of axial stress conditions. Each axial stress condition respectively corresponds to an axial stress value of the predefined axial stress path at a respective sample time of the plurality of axial strain measurements of the cement slurry.

In one embodiment of the method, solving the elastoplastic hydrating cement paste model involves first determining whether the hydrating cement paste is in the elastic or plastic domain by computing the yield function F of the model.

If the yield function is negative, the hydrating cement paste is in the elastic domain and the next axial stress condition should be selected since no additional information on the plasticity parameters can be obtained in the elastic domain.

If the yield function is positive, the hydrating cement paste is in the plastic domain and the elastoplastic hydrating cement paste model can be solved.

To solve the set of equations of the elastoplastic hydrating cement paste model, a Newton-Raphson method can be used for instance.

The solution of the elastoplastic hydrating cement paste model gives a simulated axial strain value associated with the axial stress condition.

Each simulated axial strain value of the plurality of simulated axial strain values is then compared with a respectively axial strain measurement of the plurality of axial strain measurements to determine an updated value of said plasticity parameter.

An updated value of said plasticity parameter may thus be determined to bring the simulated axial strain value closer, or equal, to the axial strain measurements.

A subsequent calibration processing operation may be performed in order to confirm the determined value of said plasticity parameter, by providing as initial value of the plasticity parameter said determined value of the plasticity parameter.

The updated value may be determined based on effects of the plasticity parameter on the simulated axial strain values that are known in the field of the invention. For instance, if the simulated axial strain value is lower than a respectively axial strain measurement and if an increase of the plasticity parameter is known, in the field of the invention, to increase the simulated axial strain values, said plasticity parameter may be determined from the initial value by increase said initial value by a predefined quantity, for instance 10%. Alternatively, a predefined range for the initial values of the plasticity parameter may be scanned in a plurality of calibration processing operations, resulting in a plurality of simulated axial strain values.

A plurality of error values, function of the distance between each simulated axial strain values and the axial strain measurements may be computed for each simulated axial strain value and the updated value of the plasticity parameter may be selected based on said plurality of error values, by selecting the initial value of the plasticity parameter leading to the smallest error value among the plurality of error values.

A single error value may be computed for each calibration processing operation of the plurality of calibration processing operations by averaging the distances between each simulated axial strain value and the respective axial strain measurement for each calibration processing operation of the plurality of calibration processing operations.

In some embodiments of the invention, the calibration processing operation is based on the evaluation of the plastic parameter on the measurements of the predefined stress path at constant axial stress and its validation and possible adjustment on the measurements on the predefined stress path comprising loading/unloading cycles.

Expressions such as "comprise", "include", "incorporate", "contain", "is" and "have" are to be construed in a non-exclusive manner when interpreting the description and its associated claims, namely construed to allow for other items or components which are not explicitly defined also to be present. Reference to the singular is also to be construed in be a reference to the plural and vice versa.

A person skilled in the art will readily appreciate that various parameters disclosed in the description may be modified and that various embodiments disclosed may be combined without departing from the scope of the invention.

The invention claimed is:

1. A method for determining a plasticity parameter of a hydrating cement paste comprising:
providing a plurality of components of a cement paste, the cement past including comprising at least cement powder and water,
mixing said plurality of components to obtain a cement slurry and pouring said cement slurry in a sealed oedometric cell,
performing at least one oedometric measurement operation comprising:
applying a predefined axial stress path to the cement slurry inside the oedometric cell, said axial stress path being a profile of axial stress applied to the cement slurry over a predefined measurement duration, and
performing a plurality of measurements of an axial strain of said cement slurry inside the oedometric cell, respectively at a plurality of respective sample times within said predefined measurement duration,
wherein said at least one oedometric measurement operation is performed within a predefined early-age time interval following the mixing of said cement slurry,
determining at least one value of a plasticity parameter of the hydrating cement paste by performing at least one calibration processing operation comprising:
providing an initial value of a plasticity parameter of an elastoplastic model of hydrating cement paste,
determining a plurality of simulated axial strain values by solving said elastoplastic model of hydrating cement paste for a plurality of respective axial stress conditions respectively corresponding to axial stress values of the predefined axial stress path at the respective
sample times of the plurality of axial strain measurements of the cement slurry, and comparing the plurality of simulated axial strain values from said at least one calibration processing operation with the plurality of axial strain measurements of the cement slurry to determine a plasticity parameter of the hydrating cement paste; and
wherein said plasticity parameter is chosen between a parameter hardening function, a parameter of a plastic yield surface and a parameter of a plastic potential of said elastoplastic model of hydrating cement paste, and
wherein solving said elastoplastic model of hydrating cement paste comprises computing a hardening function of the pastic yield surface by solving:
$dp_o - h_\xi\, d\xi - h_t d\varepsilon_{vp} = 0$
where
$\xi$ is the hydration degree;
$\varepsilon_{vp}$ is the plastic volumetric strain;
$h_\xi = (\partial p_o)/\partial\xi$ and $h_t = (\partial p_o)/(\partial\varepsilon_{ep})$ are hardening parameters;
and wherein said plasticity parameter is function of at least one of said hardening parameter $h_\xi$ and $h_t$.

2. The method according to claim 1, wherein said predefined early-age time interval following the mixing of said cement is less than 10 days, preferably less than 6 days.

3. The method according to claim 1, wherein said predefined axial stress path is a constant axial stress over the predefined measurement duration.

4. The method according to claim 1, wherein said predefined measurement duration is at least 1 day, preferably at least 4 days, more preferably 6 days.

5. The method according to claim 1, wherein said oedometric measurement operation starts less than 10 minutes after the mixing of said cement slurry.

6. The method according to claim 1, wherein said predefined axial stress path comprises at least one loading/unloading cycle in which an axial stress applied to the cement slurry varies between a predefined minimum axial stress and a predefined maximum axial stress.

7. The method according to claim 1, wherein said predefined measurement duration is less least 1 hour.

8. The method according to claim 1, wherein solving said elastoplastic model of hydrating cement paste comprises computing a plastic yield surface of a modified Cam-Clay yield surface model by solving:
$q^2 + M^2(p_d + p_t)(p_d - p_o) = 0$
Where
$p_d$ is the differential mean stress (Terzaghi effective mean stress)
$P_t$ is the yield stress related to the tensile strength of the material
$P_o$ is the yield stress under hydrostatic loading
M is the Cam-Clay parameter corresponding to the slope of the Critical State Line and wherein said plasticity parameter is function of said Cam-Clay parameter M.

9. A method according to claim 1, wherein solving said elastoplastic model of hydrating cement paste further comprises computing a poroelasticity of a cement paste derived from Hooke's law by solving:
$c_d dp_d + c_d(1-b)\chi dp_w - (d\varepsilon_v - d\varepsilon_{vp}) = 0$
$dq - G(d\gamma - d\gamma_p) = 0$ Where
- $p_d$ is the differential mean stress (Terzaghi effective mean stress)
- $p_w$ is the pore pressure
- q is the second invariant of the deviatoric stress tensor
- $\gamma$ is the shear strain intensity
- $\gamma_p$ is plastic shear strain intensity
- $\varepsilon_v$ is the volumetric strain
- $\varepsilon_{vp}$ is the plastic volumetric strain
- $c_d = 1/K_d$ is the drained compressibility of the porous material
- b is Biot's effective stress coefficient
- $\chi$ is the Bishop effective stress coefficient
- G is the elastic shear modulus and wherein said poroelasticity parameters $c_d$, b, $\chi$ and G are determined by using an upscaling technique.

10. A method according to claim 1, further including repeating said calibration processing operation a plurality of times with a respective plurality of initial values of the plasticity parameter, said plurality of initial values of the plasticity parameter scanning a predefined range of initial value of the plasticity parameter, and wherein comparing the plurality of simulated axial strain values from said plurality of calibration processing operations with the plurality of axial strain measurements of the cement slurry comprises computing a plurality of error values, respectively associated to each simulated axial strain values and the value of the plasticity parameter may be determined from said plurality of error values, in particular by selecting the initial value of the plasticity parameter leading to the smallest error value among the plurality of error values.

11. A non-transitory computer readable storage medium, having stored thereon a computer program comprising program instructions, the computer program being loadable into a data-processing unit and adapted to cause the data-processing unit to carry out the steps of claim 1 when the computer program is run by the data-processing device.

* * * * *